United States Patent [19]

Seele et al.

[11] Patent Number: 4,940,717

[45] Date of Patent: Jul. 10, 1990

[54] FUNGICIDAL IMIDAZOLYLMETHYLOXIRANES

[75] Inventors: Rainer Seele, Fussgoenheim; Stefan Karbach, Neustadt; Bernd Janssen, Ludwigshafen; Reiner Kober, Fussgoenheim; Eberhard Ammermann, Ludwigshafen; Gisela Lorenz, Neustadt, all of Fed. Rep. of Germany

[73] Assignee: BASF Aktiengesellschaft, Ludwigshafen, Fed. Rep. of Germany

[21] Appl. No.: 319,318

[22] Filed: Mar. 6, 1989

[30] Foreign Application Priority Data

Mar. 10, 1988 [DE] Fed. Rep. of Germany ....... 3807951

[51] Int. Cl.$^5$ .................. A01N 43/50; C07D 405/06; C07D 405/14
[52] U.S. Cl. .................... 514/341; 514/397; 546/278; 548/336
[58] Field of Search ............ 548/336; 546/278; 514/341, 397

[56] References Cited

U.S. PATENT DOCUMENTS

| | | | |
|---|---|---|---|
| 4,464,381 | 8/1984 | Janssen et al. | 514/383 |
| 4,518,415 | 5/1985 | Marchington et al. | 71/92 |
| 4,652,580 | 3/1987 | Janssen et al. | 514/383 |

FOREIGN PATENT DOCUMENTS 3218130 11/1983 Fed. Rep. of Germany .
3536529 4/1987 Fed. Rep. of Germany .

OTHER PUBLICATIONS

Chemical Abstracts, 106:38472a (1987), [Ger. Offen. 3,511,411 Janssen et al., 10/2/86].
Chemical Abstracts, 100:85704p (1984), [Ger. Offen. 3,218,130, Janssen et al., 11/17/83].

Primary Examiner—Richard A. Schwartz
Attorney, Agent, or Firm—Oblon, Spivak, McClelland, Maier & Neustadt

[57] ABSTRACT

Imidazolylmethyloxiranes of the general formula I

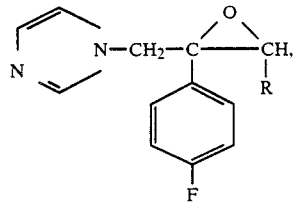

where R is phenyl, pyridyl, tetrahydropyranyl, norbornyl, $C_3$–$C_{12}$-cycloalkyl or $C_5$–$C_8$-cycloalkenyl, these radicals being unsubstituted or substituted, and their plant-tolerated acid addition salts and metal complexes, and fungicides containing these compounds.

7 Claims, No Drawings

FUNGICIDAL IMIDAZOLYLMETHYLOXIRANES

The present invention relates to novel imidazole compounds, processes for their preparation and fungicides containing these compounds.

It is known that azolylmethyloxiranes which are substituted by halophenyl can be used as fungicides (DE-3 218 130.2 and DE-3 536 529.3). However, their fungicidal action is unsatisfactory.

We have found that compounds of the general formula I

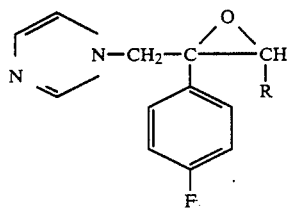

where R is phenyl, pyridyl, tetrahydropyranyl, norbornyl, $C_3$–$C_{12}$-cycloalkyl or $C_5$–$C_8$-cycloalkenyl, these radicals being unsubstituted or monosubstituted to trisubstituted by halogen, nitro, phenoxy, alkyl, amino, alkoxy, haloalkoxy or haloalkyl, each of 1 to 4 carbon atoms, or their plant-tolerated acid addition salts or metal complexes have a better fungicidal action, in particular against botrytis diseases, than the known triazole compounds.

The compounds of the formula I contain chiral centers and are generally obtained in the form of racemates or diastereomer mixtures of erythro or threo forms. In the case of the novel compounds, the erythro or threo diastereomers can be separated in a conventional manner, for example on the basis of their different solubilities or by column chromatography and can be isolated in pure form. An isolated diastereomer of this type can be converted into pure enantiomers by a conventional method. Both the pure diastereomers or enantiomers and their mixtures obtained in the synthesis can be used as fungicides The present invention embraces both the individual compounds and their mixtures.

Imidazolylmethyloxiranes of the formula I, where R is phenyl which is unsubstituted or substituted by one or two substituents from the group consisting of fluorine, chlorine, bromine and trifluoromethyl, are preferred. Compounds in which R is fluorophenyl or chlorophenyl are particularly preferred.

R is, for example, phenyl, halophenyl, 2-chlorophenyl, 2-fluorophenyl, 2-bromophenyl, 3-chlorophenyl, 3-bromophenyl, 3-fluorophenyl, 2,6-difluorophenyl, 4-fluorophenyl, 4-chlorophenyl, 4-bromophenyl, 2,4-dichlorophenyl, 2,3-dichlorophenyl, 2,5-dichlorophenyl, 2,6-dichlorophenyl, 2-chloro-6-fluorophenyl, alkoxyphenyl, 2-methoxyphenyl, 3-methoxyphenyl, 4-methoxyphenyl, 4-trifluoromethoxyphenyl, 2,4-dimethoxyphenyl, alkylphenyl, 4-ethylphenyl, 4-isopropylphenyl, 4-tertbutylphenyl, 4-tert-butoxyphenyl, 2-chloro-4-fluorophenyl, 2-chloro-6-methylphenyl, 3,4-dimethoxyphenyl, 3-phenoxyphenyl, 4-phenoxyphenyl, 3-nitrophenyl, 4-nitrophenyl, 3-aminophenyl, 4-aminophenyl, 2-trifluoromethylphenyl, 3-trifluoromethylphenyl, 4-trifluoromethylphenyl, cyclopropyl, cyclobutyl, cyclopentyl, cyclohexyl, cyclooctyl, cyclododecyl, 4-tetrahydropyranyl, 2-cyclohexenyl, 3-cyclohexenyl, norbornyl and 3-pyridyl. Acid addition salts are salts with inorganic or organic acids, for example the hydrochlorides, bromides, sulfates, nitrates, phosphates, oxalates or dodecylbenzenesulfonates. The activity of the salts is due to the cation, so that in general any anion may be chosen. The novel active ingredient salts are prepared by reacting the imidazolylmethyloxiranes (I) with the acids.

Metal complexes of the active ingredients I or their salts can be formed, for example, with copper, zinc, tin, manganese, iron, cobalt or nickel, by reacting the imidazolylmethyloxiranes with corresponding metal salts, for example with copper sulfate, zinc chloride or tin chloride.

The compounds of the formula I can be prepared, for example, (a) by reacting a compound of the formula II

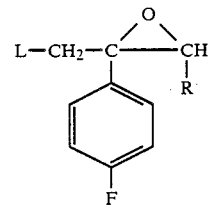

where R has the abovementioned meanings and L is a leaving group which can be nucleophilically substituted (halogen or OH), with a compound of the formula III

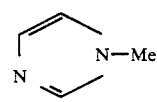

where Me is hydrogen or a metal atom (Na or K) or trimethylsilyl, or (b) converting a compound of the formula IV

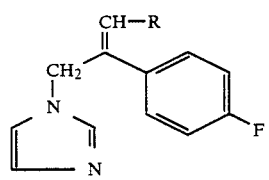

where R has the stated meanings, into an epoxide. Where Me is hydrogen, reaction (a) is carried out in the presence or absence of a solvent or diluent and with or without the addition of an inorganic or organic base and of a reaction accelerator, at from 10° to 120° C. The preferred solvents and diluents include ketones, such as acetone, methyl ethyl ketone or cyclohexanone, nitriles, such as acetonitrile or propionitrile, alcohols, such as methanol, ethanol, iso-propanol, n-butanol or glycol, esters, such as ethyl acetate, methyl acetate or butyl acetate, ethers, such as tetrahydrofuran, diethyl ether, dimethoxyethane, dioxane or diisopropyl ether, amides, such as dimethylformamide, dimethylacetamide or N-methylpyrrolidone, and dimethyl sulfoxide, sulfolane or mixtures of these.

Examples of suitable bases, which may also be used as acid acceptors in the reaction, are alkali metal hydroxides, such as lithium hydroxide, sodium hydroxide or potassium hydroxide, alkali metal carbonates, such as sodium carbonate, potassium carbonate or cesium carbonate or sodium bicarbonate, potassium bicarbonate or cesium bicarbonate, pyridine or 4-dimethylaminopyridine. However, other conventional bases may also be used.

Preferred reaction accelerators are metal halides, such as sodium iodide or potassium iodide, quaternary ammonium salts, such as tetrabutylammonium chloride, bromide, iodide or bisulfate, benzyltriethylammonium chloride or bromide, or crown ethers, such as 12-crown-4, 15-crown-5, 18-crown-6, dibenzo-18-crown-6 or dicyclohexano-18-crown-6.

The reaction is generally carried out at from 20° to 150° C., under atmospheric or superatmospheric pressure, continuously or batchwise.

If Me is a metal atom, then reaction (a) is carried out in the presence or absence of a solvent or diluent and with or without the addition of a strong inorganic or organic base, at from −10° to 120° C. The preferred solvents and diluents include amides, such as dimethylformamide, diethylformamide, dimethylacetamide, diethylacetamide, N-methylpyrrolidone and hexamethylphosphorotriamide. and sulfoxides, such as dimethyl sulfoxide and sulfolane.

Examples of suitable bases, which may also be used as acid acceptors in the reaction, are alkali metal hydrides, such as lithium hydride, sodium hydride and potassium hydride, alkali metal amides, such as sodium amide and potassium amide, and sodium tert-butoxide, potassium tert-butoxide, triphenylmethyllithium, triphenylmethylsodium, triphenylmethylpotassium, naphthalenelithium, naphthalenesodium and naphthalenepotassium.

Suitable diluents for reaction (b) are polar organic solvents, such as nitriles, eg. acetonitrile, sulfoxides, eg. dimethyl sulfoxide, formamides, eg. dimethylformamide, ketones, eg. acetone, ethers, eg. diethyl ether or tetrahydrofuran, and in particular chlorohydrocarbons, eg. methylene chloride and chloroform.

The reaction is generally carried out at from 0° to 100° C., preferably from 20° to 80° C. When a solvent is present, the reaction is advantageously carried out at the boiling point of the particular solvent.

The novel starting compounds II are obtained by epoxidation of the corresponding olefins V:

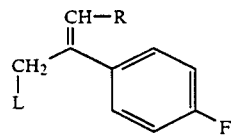

(cf. G. Dittus in Houben-Weyl-Müller, Methoden der Organischen Chemie, Georg Thieme Verlag, Stuttgart, 1965, Vol. VI, 3, page 385 et seq.).

Compound V is prepared by halogenating or oxidizing an olefin of the formula VI

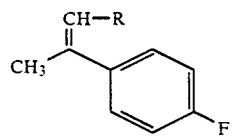

in the allyl position by a known method.

Examples of suitable halogenating reagents are N-chloro- and N-bromosuccinimide in halohydrocarbons, such as carbon tetrachloride, trichloroethane or methylene chloride, at from 20° to 100° C. Allyl oxidation is carried out using, for example, peresters, such as tertbutyl perbenzoate, in the presence of a heavy metal salt, eg. copper(I) chloride or copper(I) bromide. The reaction is carried out in an inert solvent at from 10° to 100° C.

The allyl halides or alcohols V thus obtained are then converted into the corresponding epoxides II (L=halogen or OH). For this purpose, the olefins V are oxidized with peroxycarboxylic acids, such as perbenzoic acid, 3-chlorobenzoic acid, 4-nitroperbenzoic acid, monoperphthalic acid, peracetic acid, perpropionic acid, permaleic acid, monopersuccinic acid, perpelargonic acid or trifluoroperacetic acid, in an inert solvent, preferably a chlorohydrocarbon, eg. methylene chloride, chloroform, carbon tetrachloride or dichloroethane or, if required, in acetic acid, ethyl acetate, acetone or dimethylformamide, in the presence or absence of a buffer, such as sodium acetate, sodium carbonate or disodium hydrogen phosphate. The reaction is carried out at from 10° to 100° C. and, if required, is catalyzed with, for example, iodine, sodium tungstate or light. Alkaline solutions of hydrogen peroxide (about 30% strength) in methanol, ethanol, acetone or acetonitrile at from 25° to 30° C. and alkyl hydroperoxides, eg. tert-butyl hydroperoxide, with the addition of a catalyst, eg. sodium tungstate, pertungstic acid, molybdenum hexacarbonyl or vanadyl acetylacetonate, are also suitable for the oxidation. Some of the stated oxidizing agents can be produced in situ.

While the resulting epoxyhalides II (L=halogen) according to process (a) can be further reacted, the corresponding epoxyalcohols II (L=OH) are converted into reactive esters, which are then reacted with the compounds III according to process (a).

The reactive esters which are reacted with III are prepared by generally known methods (Houben-Weyl-Müller, Methoden der organischen Chemie, Georg Thieme Verlag, Stuttgart, 1955, Volume 9, pages 388, 663 and 671). Such esters are, for example, methanesulfonates, trifluoromethanesulfonates, 2,2,2-trifluoroethanesulfonates, nonafluorobutanesulfonates, 4-methylbenzenesulfonates, 4-bromobenzenesulfonates, 4-nitrobenzenesulfonates and benzenesulfonates.

The compounds V can be prepared by generally known processes of olefin synthesis (Houben-Weyl-Müller, Methoden der organischen Chemie, Georg Thieme Verlag, Stuttgart, 1972, Vol. V, 1b).

The Examples which follow illustrate the preparation of the active ingredients.

I. Preparation of the starting materials

Method A 8.4 g of sodium hydroxide in 40 ml of water are added to a solution of 85.5 g of 2-trifluoromethylbenzaldehyde in 300 ml of methanol. The reaction mixture is cooled to 10° C., and 69 g of 4-fluorophenylacetaldehyde are rapidly added dropwise, the temperature of the solution not exceeding 30° C. Stirring is carried out for 2 hours at room temperature (20° C.), after which 300 ml of water are added to the colorless reaction solution and the resulting emulsion is extracted by shaking with methyl tert-butyl ether. The organic phase is separated off, dried over sodium sulfate and evaporated down under reduced pressure. In the subsequent distillation of the remaining residue, 96 g (65%) of E-2-(4-fluorophenyl)-3-(2-trifluoromethylphenyl)-propenal are obtained under 0.3 mbar and at a distillation temperature of 116° C.

Method B 96 g of E-2-(4-fluorophenyl)-3-(2-trifluoromethylphenyl)-propenal are dissolved in 300 ml of methanol and 2.3 ml of concentrated sodium hydroxide solution are added. The reaction solution is stirred at 0° C. while 27.7 g of hydrogen peroxide (about 50% strength) are slowly added dropwise, the internal temperature not exceeding 30° C. When the addition is complete, stirring is continued for 6 hours at room temperature, after which 5 g of sodium borohydride which has been dissolved in a little 10% strength sodium hydroxide solution are added. After the reaction mixture has been stirred for 18 hours at room temperature, 100 ml of water are added to the solution, and the resulting emulsion is extracted by shaking with methylene chloride. The organic phase isolated is then dried over sodium sulfate and evaporated down. 90 g (89%) of cis-2-hydroxymethyl-2-(4-fluorophenyl)-3-(2-trifluoromethylphenyl)-oxirane are obtained.

Method C 61 g of 4-methylbenzenesulfonyl chloride are added, at room temperature, to a solution of 90 g of cis-2-hydroxymethyl-2-(4-fluorophenyl)-3-(2-trifluoromethylphenyl)-oxirane in 300 ml of methylene chloride and 58 g of triethylamine. After 24 hours, the reaction mixture is washed with aqueous sodium bicarbonate solution and water, dried over sodium sulfate and evaporated down under reduced pressure. 128.4 g (95%) of cis-2-(4-methylphenylsulfonyloxymethyl)-2-(4-fluorophenyl)-3-(2-trifluoromethylphenyl)-oxirane are obtained from the residue.

II. Preparation of the end products

EXAMPLE 1

27.3 g of imidazole and 9.5 g of sodium hydride (80% strength dispersion in mineral oil) are suspended in 300 ml of N,N-dimethylformamide, and a solution of 128.4 g of cis-2-(4-methylphenylsulfonyloxymethyl)-2-(4-fluorophenyl)-3-(2-trifluoromethylphenyl)-oxirane in 200 ml of N,N-dimethylformamide is added at room temperature. After 8 hours, the reaction solution is poured onto water and extracted with methyl tert-butyl ether. The organic phase is washed with water, and dried over sodium sulfate, and the solvent is evaporated off under reduced pressure. 94 g of cis-2-imidazolylmethyl-2-(4-fluorophenyl)-3-(2-trifluoromethylphenyl)oxirane of melting point 127°-135° C. are obtained from methyl tert-butyl ether/n-hexane (compound No. 1).

The compounds listed in the Table can be prepared similarly to Example 1.

TABLE

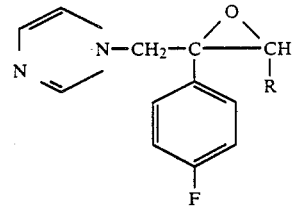

| No. | R | Isomer | M.p. |
|---|---|---|---|
| 1 | 2-CF$_3$—C$_6$H$_4$ | cis | 127–135° C. |
| 2 | 3-CF$_3$—C$_6$H$_4$ | cis | |
| 3 | 4-CF$_3$—C$_6$H$_4$ | cis | |
| 4 | 2-OCH$_3$—C$_6$H$_4$ | cis | resin |
| 5 | 3-OCH$_3$—C$_6$H$_4$ | cis | |
| 6 | 4-OCH$_3$—C$_6$H$_4$ | cis | |
| 7 | 2-Cl—C$_6$H$_4$ | cis | 119–122° C. |
| 8 | 3-Cl—C$_6$H$_4$ | cis | resin |
| 9 | 4-Cl—C$_6$H$_4$ | cis | |
| 10 | 2,4-Cl$_2$—C$_6$H$_3$ | cis | |
| 11 | 2-Cl-4-F—C$_6$H$_3$ | cis | 135° C. |
| 12 | 2,3-Cl$_2$—C$_6$H$_3$ | cis | |
| 13 | 2,5-Cl$_2$—C$_6$H$_3$ | cis | |
| 14 | 2,6-Cl$_2$—C$_6$H$_3$ | cis | |
| 15 | 2-Cl-6-F—C$_6$H$_3$ | cis | |
| 16 | 2-F—C$_6$H$_4$ | cis | |
| 17 | 3-F—C$_6$H$_4$ | cis | |
| 18 | 4-F—C$_6$H$_4$ | cis | |
| 19 | 2-Br—C$_6$H$_4$ | cis | 122–124° C. |
| 20 | 3-Br—C$_6$H$_4$ | cis | |
| 21 | 4-Br—C$_6$H$_4$ | cis | |
| 22 | 3-NO$_2$—C$_6$H$_4$ | cis | |
| 23 | 4-NO$_2$—C$_6$H$_4$ | cis | |
| 24 | 3-NH$_2$—C$_6$H$_4$ | cis | |
| 25 | 4-NH$_2$—C$_6$H$_4$ | cis | |
| 26 | 2-Cl-5-NO$_2$—C$_6$H$_3$ | cis | |
| 27 | 2,4-OCH$_3$—C$_6$H$_3$ | cis | |
| 28 | 3,4-OCH$_3$—C$_6$H$_3$ | cis | |
| 29 | 4-C$_2$H$_5$—C$_6$H$_4$ | cis | |
| 30 | 4-tert.butyl-C$_6$H$_4$ | cis | |
| 31 | 4-O-tert.butyl-C$_6$H$_4$ | cis | |
| 32 | 4-O-phenyl-C$_6$H$_4$ | cis | |
| 33 | 3-O-phenyl-C$_6$H$_4$ | cis | |
| 34 | 3-pyridyl | cis | |
| 35 | cyclopropyl | cis | |
| 36 | cyclobutyl | cis | |
| 37 | cyclopentyl | cis | |
| 38 | cyclohexyl | cis | IR: 2928, 2853, 1510, 1450, 1227, 838 cm$^{-1}$ |
| 39 | 3-cyclohexenyl | cis | |
| 40 | 3-cyclopentenyl | cis | |
| 41 | norbornyl | cis | |
| 42 | 4-tetrahydropyranyl | cis | |
| 43 | 3-tetrahydropyranyl | cis | |
| 44 | C$_6$H$_5$ | cis | |
| 45 | 4-OCF$_3$—C$_6$H$_4$ | cis | resin |
| 46 | 2,6-F$_2$—C$_6$H$_3$ | cis | 182–188° C. |

In general terms, the novel compounds are extremely effective on a broad spectrum of phytopathogenic fungi, in particular those from the class consisting of the Ascomycetes and Basidiomycetes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:
*Erysiphe graminis* in cereals,

*Erysiphe cichoracearum* and *Sphaerotheca fuliginea* in cucurbits,
*Podosphaera leucotricha* in apples,
*Uncinula necator* in vines,
Puccinia species in cereals,
Rhizoctonia solani in cotton,
Ustilago species in cereals and sugar cane,
*Venturia inaequalis* (scab) in apples,
Helminthosporium species in cereals,
*Septoria nodorum* in wheat,
*Botrytis cinerea* (gray mold) in strawberries and grapes,
*Cercospora arachidicola* in groundnuts,
*Pseudocercosporella herpotrichoides* in wheat and barley,
*Pyricularia oryzae* in rice,
Phytophthora infestans in potatoes and tomatoes,
Fusarium and Verticillium species in various plants,
*Plasmopara viticola* in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene), chlorinated aromatics (e.g., chlorobenzenes), paraffins (e.g., crude oil fractions), alcohols (e.g., methanol, butanol), ketones (e.g., cyclohexanone), amines (e.g., ethanolamine, dimethylformamide), and water; carriers such as ground natural minerals (e.g., kaolins, aluminas, talc and chalk) and ground synthetic minerals (e.g, highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicides generally contain from 0.1 to 95, and preferably from 0.5 to 90, wt% of active ingredient. The application rates are from 0.02 to 3 kg or more of active ingredient per hectare, depending on the type of effect desired. The novel compounds may also be used for protecting materials, e.g., on *Paecilomyces variotii*.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 7 is mixed with 10 parts by weight of N-methyl-α-pyrrolidone. A mixture is obtained which is suitable for application in the form of very fine drops.

II. 20 parts by weight of compound no. 11 is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 7 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 11 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 7 is well mixed with 3 parts by weight of the sodium salt of diisobutylnaphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in water, a spray liquor is obtained.

VI. 3 parts by weight of compound no. 11 is intimately mixed with 97 parts by weight of particulate kaolin. A dust is obtained containing 3% by weight of the active ingredient.

VII. 30 parts by weight of compound no. 7 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 11 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 7 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in a greater fungicidal action spectrum.

The following list of fungicides with which the novel compounds may be combined is intended to illustrate possible combinations but not to impose any restrictions.

Examples of fungicides which may be combined with the novel compounds are:
sulfur,
dithiocarbamates and their derivatives, such as
ferric dimethyldithiocarbamate,
zinc dimethyldithiocarbamate, zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate,
zinc N,N'-propylenebisdithiocarbamate and
N,N'-polypropylenebis(thiocarbamyl) disulfide;
nitro derivatives, such as
dinitro(1-methylheptyl)-phenyl crotonate,
2-sec-butyl-4,6-dinitrophenyl 3,3-dimethylacrylate,
2-sec-butyl-4,6-dinitrophenyl isopropylcarbonate and
diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1-[-bis-(dimethylamino)-phosphinyl]-3-phenyl-1,2,4-triazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-(fur-2-yl)-benzimidazole,
2-(thiazol-4-yl)benzimidazole,
N-(1,1,2,2-tetrachloroethylthio)-tetrahydrophthalimide,
N-trichloromethylthiotetrahydrophthalimide,
N-trichloromethylthiophthalimide,
N-dichlorofluoromethylthio-N',N'-dimethyl-N-phenyl-sulfuric acid diamide,
5-ethoxy-3-trichloromethyl-1,2,3-thiadiazole,
2-thiocyanatomethylthiobenzothiazole,
1,4-dichloro-2,5-dimethoxybenzene,
4-(2-chlorophenylhydrazono)-3-methyl-5-isoxazolone,
2-thiopyridine 1-oxide,
8-hydroxyquinoline and its copper salt,
2,3-dihydro-5-carboxanilido-6-methyl-1,4-oxathiyne,
2,3-dihydro-5-carboxanilido-6-methyl-1,4-oxathiyne 4,4-dioxide,
2-methyl-5,6-dihydro-4H-pyran-3-carboxanilide,
2-methylfuran-3-carboxanilide,
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl)-formamide),
1-(3,4-dichloroanilino)-1-formylamino-2,2,2-trichloroethane,
2,6-dimethyl-N-tridecylmorpholine and its salts,
2,6-dimethyl-N-cyclododecylmorpholine and its salts,
N-[3-(p-tert.-butylphenyl)-2-methylpropyl]-cis-2,6-dimethylmorpholine,
N-[3-(p-tert.-butylphenyl)-2-methylpropyl]-piperidine,
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one,
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α-(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene,
1,2-bis-(3-methoxycarbonyl-2-thioureido)-benzene, and
various fungicides, such as
dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-(ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazol-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

Use examples

For comparison purposes, cis-2-(1,2,4-triazol-1-ylmethyl)-2-(4-chlorophenyl)-3-phenyloxirane (A)-disclosed in DE-3 218 130.2—and cis-2-(1,2,4-triazol-1-ylmethyl)-2-(4-fluorophenyl)-3-(2-chlorophenyl)-oxirane—disclosed in DE-3 536 529.3—were used.

Use Example 1

Action on *Plasmopara viticola*

Leaves of potted vines of the Müller-Thurgau variety were sprayed with aqueous suspensions containing (dry basis) 80% of active ingredient and 20% of emulsifier. To assess the duration of action, the plants were set up, after the sprayed-on layer had dried, for 8 days in the greenhouse. Then the leaves were infected with a zoospore suspension of *Plasmopara viticola*. The plants were first placed for 48 hours in a water vapor-saturated chamber at 24° C. and then in a greenhouse for 5 days at from 20° to 30° C. To accelerate and intensify the sporangiophore discharge, the plants were then again placed in the moist chamber for 16 hours. The extent of fungus attack was then assessed on the undersides of the leaves.

The results show that active ingredients 7 and 11, applied as 0.05% spray liquors, have a better fungicidal action (90%) than prior art comparative agent A (50%).

Use Example 2

Action on *Botrytis cinerea*

In the open, small plots of strawberry plants of the "Senga-Sengana" variety were treated during the main period of bloom. Two days later, the plants in all the plots were inoculated with a spore suspension of *Botrytis cinerea*. After a further five days, the plots were treated again. 38 days later the ripe strawberries were checked for Botrytis attack.

The results show that active ingredient 7, at an application rate of 2 kg/ha, has a better fungicidal action (73%) than prior art active ingredient B (0%).

We claim:

1. An imidazolylmethyloxirane of the formula I

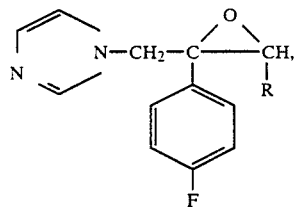

where R is phenyl, pyridyl, tetrahydropyranyl, norbornyl, $C_3$–$C_{12}$-cycloalkyl or $C_5$–$C_8$-cycloalkenyl, these radicals being unsubstituted or substituted by halogen, nitro, phenoxy, alkyl, amino, alkoxy, haloalkoxy or haloalkyl, where alkyl is of 1 to 4 carbon atoms, or a plant-tolerated acid addition salt or metal complex thereof.

2. A compound of the formula I as set forth in claim 1, R denoting phenyl which is unsubstituted or bears one or two substituents selected from the group consisting of fluorine, chlorine, bromine or trifluoromethyl.

3. A compound of the formula I as set forth in claim 1, R denoting fluorophenyl or chlorophenyl.

4. A compound as set forth in claim 1, where R is 2-chlorophenyl and the compound is in the cis-form.

5. A compound as set forth in claim 1, where R is 2-chloro-4-fluorophenyl and the compound is in the cis-form.

6. A fungicidal agent containing a fungicidally effective amount of an imidazolylmethyloxirane of the formula I

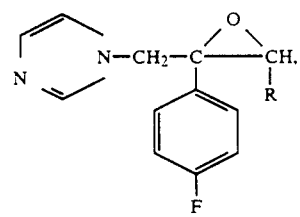

where R is phenyl, pyridyl, tetrahydropyranyl, norbornyl, $C_3$–$C_{12}$-cycloalkyl or $C_5$–$C_8$-cycloalkenyl, these radicals being unsubstituted or substituted by halogen, nitro, phenoxy, alkyl, amino, alkoxy, haloalkoxy or haloalkyl, where alkyl is of 1 to 4 carbon atoms, or a plant-tolerated acid addition salt or metal complex thereof, and an inert additive.

7. A method for combating fungi, wherein a fungicidally effective amount of an imidazolylmethyloxirane of the formula I

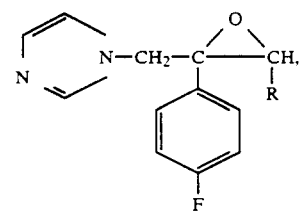

where R is phenyl, pyridyl, tetrahydropyranyl, norbornyl, $C_3$–$C_{12}$-cycloalkyl or $C_5$–$C_8$-cycloalkenyl, these radicals being unsubstituted or substituted by halogen, nitro, phenoxy, alkyl, amino, alkoxy, haloalkoxy or haloalkyl, where alkyl is of 1 to 4 carbon atoms, or a plant-tolerated acid addition salt or metal complex thereof, is allowed to act on the fungi, or on materials, areas, plants or seed threatened by fungus attack.

* * * * *